(12) United States Patent
Drapeau

(10) Patent No.: US 7,526,071 B2
(45) Date of Patent: Apr. 28, 2009

(54) SYSTEM AND METHOD FOR PATIENT BALANCE AND POSITION ANALYSIS

(75) Inventor: Scott James Drapeau, Cordova, TN (US)

(73) Assignee: Warsaw Orthopedic, Inc.

( * ) Notice: Subject to any disclaimer, the term of this patent is extended or adjusted under 35 U.S.C. 154(b) by 104 days.

(21) Appl. No.: 11/697,426

(22) Filed: Apr. 6, 2007

(65) Prior Publication Data

US 2008/0245972 A1    Oct. 9, 2008

(51) Int. Cl.
*G21K 4/00* (2006.01)
*G01N 23/083* (2006.01)
*H05G 1/28* (2006.01)

(52) U.S. Cl. .................... 378/163; 378/62; 378/165; 378/192

(58) Field of Classification Search .............. 378/4, 378/20, 21, 37, 51, 62, 63, 163, 165, 177, 378/180, 189, 192, 195, 196, 204, 208, 210; 600/425–427
See application file for complete search history.

(56) References Cited

U.S. PATENT DOCUMENTS

| | | | |
|---|---|---|---|
| 3,906,931 A | 9/1975 | Terekhov | |
| 4,719,646 A * | 1/1988 | Saunders et al. | ............ 378/179 |
| 4,971,069 A | 11/1990 | Gracovetsky | |
| 5,114,240 A | 5/1992 | Kindt-Larsen et al. | |
| 5,209,240 A | 5/1993 | Jain et al. | |
| 5,337,757 A | 8/1994 | Jain et al. | |
| 5,388,591 A | 2/1995 | De Luca et al. | |
| 5,609,162 A | 3/1997 | Blumentritt et al. | |
| 5,755,675 A | 5/1998 | Sihvonen | |
| 5,987,982 A | 11/1999 | Wenman et al. | |
| 6,056,671 A | 5/2000 | Marmer | |
| 6,063,046 A | 5/2000 | Allum | |
| 6,120,174 A | 9/2000 | Hoag et al. | |
| 6,223,067 B1 * | 4/2001 | Vilsmeier et al. | ............ 600/426 |
| 6,231,527 B1 | 5/2001 | Sol | |

(Continued)

FOREIGN PATENT DOCUMENTS

EP    0119660 A1    9/1984

(Continued)

OTHER PUBLICATIONS

Zebris, zebris Force Measuring Platform, The World of Biomechanics, zebris Medical GmbH, Max-Eyth-Weg 42 (1 page).

(Continued)

*Primary Examiner*—Edward J Glick
*Assistant Examiner*—Thomas R Artman
(74) *Attorney, Agent, or Firm*—Haynes and Boone, LLP

(57) ABSTRACT

The present disclosure is directed to systems and methods for obtaining patient balance and anatomical positioning data for use in patient treatment. More particularly, in one aspect the present disclosure is directed toward a patient analysis system for obtaining radiographic images, center-of-balance data, and anatomical positioning data of a patient for use in planning and monitoring the treatment of a patient. In one aspect, the present disclosure provides a portable patient analysis system. In another aspect, the present disclosure provides methods of using patient analysis systems having a radiographic system, a balance system, and a positioning system.

31 Claims, 10 Drawing Sheets

U.S. PATENT DOCUMENTS

| | | |
|---|---|---|
| 6,348,055 B1 | 2/2002 | Preissman |
| 6,437,257 B1 | 8/2002 | Yoshida |
| 6,502,608 B1 | 1/2003 | Burchett et al. |
| 6,514,219 B1 | 2/2003 | Guimond et al. |
| 6,611,141 B1 * | 8/2003 | Schulz et al. ............... 324/226 |
| 6,641,587 B2 | 11/2003 | Scribner et al. |
| 6,665,555 B2 * | 12/2003 | Henderson et al. .......... 600/427 |
| 6,788,968 B2 * | 9/2004 | Pettibon ...................... 600/427 |
| 6,832,987 B2 | 12/2004 | David et al. |
| 6,962,568 B1 | 11/2005 | Morger |
| 6,969,360 B1 | 11/2005 | Pai et al. |
| 7,018,089 B2 | 3/2006 | Wenz et al. |
| 7,107,832 B2 | 9/2006 | Blumentritt et al. |
| 7,361,150 B2 * | 4/2008 | Berthonnaud et al. ....... 600/595 |
| 2002/0173723 A1 | 11/2002 | Lewis et al. |
| 2002/0191487 A1 | 12/2002 | Sand |
| 2003/0004438 A1 | 1/2003 | Berthonnaud et al. |
| 2003/0181791 A1 | 9/2003 | Thomas et al. |
| 2003/0181830 A1 | 9/2003 | Guimond et al. |
| 2003/0208109 A1 | 11/2003 | David et al. |
| 2004/0228510 A1 | 11/2004 | Berthonnaud et al. |
| 2004/0260156 A1 | 12/2004 | David et al. |

FOREIGN PATENT DOCUMENTS

| | | |
|---|---|---|
| WO | WO0150956 A1 | 7/2001 |

OTHER PUBLICATIONS

Zebris, zebris Real Time Motion Analysis, The World of Biomechanics, zebris Medical GmbH, Max-Eyth-Weg 42 (1 page).

* cited by examiner

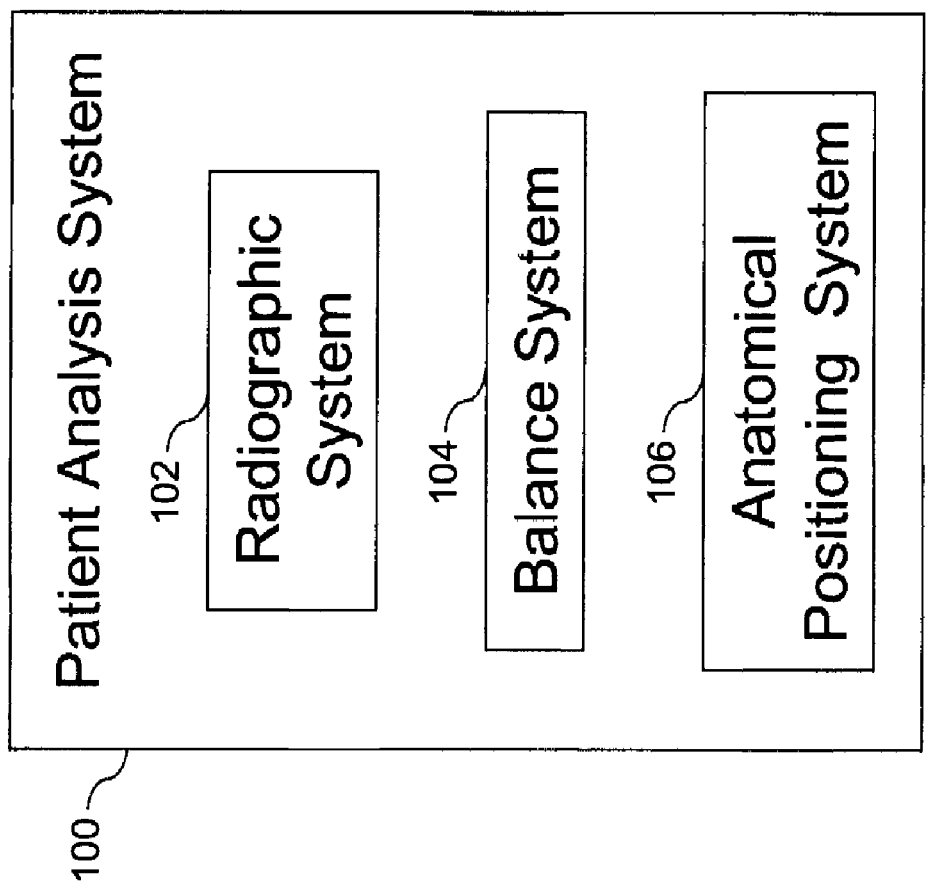

SYSTEM AND METHOD FOR PATIENT BALANCE AND POSITION ANALYSIS

BACKGROUND

The present disclosure is directed to systems and methods for obtaining patient balance and anatomical positioning data for use in planning and monitoring patient treatment. More particularly, in one aspect the present disclosure is directed toward a medical system for obtaining radiographic, center-of-balance, and anatomical positioning data of a patient for use in planning and monitoring the treatment of a patient.

Although existing systems and methods used in research and hospital settings have been generally adequate for their intended purposes, they have not been entirely satisfactory in terms of combining radiographic, center of gravity, and patient anatomical positioning data.

SUMMARY

The present disclosure provides a patient analysis system and methods of using the patient analysis system.

In another aspect, the present disclosure provides a patient analysis system. The patient analysis system includes a platform for supporting a patient. The patient analysis system also includes a radiographic system for providing radiographic images of at least a portion of a patient's skeletal structure while the patient stands on the platform. The patient analysis system also includes a balance system for determining a patient's center-of-balance while the patient stands on a center-of-gravity pressure pad, wherein the balance system determines the patient's center-of-balance at least partially based on the patient's weight distribution. The patient analysis system also includes an anatomical positioning system for providing three-dimensional positioning data for at least one of the patient's anatomical structures while the patient stands on the platform.

In another aspect, the present disclosure provides a patient analysis system. The patient analysis system includes an elongated post and a platform rotatably connected to the post. The platform is for supporting a patient. The patient analysis system also includes a radiographic system for providing radiographic images of at least a portion of a patient's skeletal structure while standing on the platform. The radiographic system includes at least one bead array movably connected to the post. The patient analysis system also includes a balance system for determining a patient's center-of-balance while standing on a center-of-gravity pressure pad. The balance system includes a force sensing pad positioned on the platform. The patient analysis system also includes an anatomical positioning system for providing three-dimensional positioning data for at least one of the patient's anatomical structures while standing on the platform. The anatomical positioning system includes an electro-magnetic field generator, infrared camera(s), and/or video camera(s) positioned within range of the platform. One or more of these exemplary anatomical positioning systems may be selected depending on such factors as ease of use in a given situation, cost, 3D position accuracy needs, physician preference, and/or other factors.

In another aspect, the present disclosure provides a portable patient analysis system for use with a radiographic system of a medical facility. The portable system includes a platform for supporting a patient and an elongated post connectable to the platform. A bead array plate including radio-paque markers is connectable to the post. The portable system also includes a balance system for determining a patient's center-of-gravity while standing on the platform. The balance system includes a force sensing pad configured for placement on the platform. The portable system also includes an anatomical positioning system for providing three-dimensional positioning data for one or more of the patient's external and/or internal anatomical structures while standing on the platform. The anatomical positioning system includes an electro-magnetic field generator, infrared camera(s), and/or video camera(s) configured for placement within range of the platform. Again, one or more of these exemplary anatomical positioning systems may be selected depending on such factors as ease of use in a given situation, cost, 3D position accuracy needs, physician preference, and/or other factors.

In another aspect, the present disclosure provides a method of obtaining patient data. The method includes providing a patient analysis system. The patient analysis system includes a radiographic system for providing radiographic images of at least a portion of a patient's skeletal structure, a balance system including a force sensing pad for determining a patient's center-of-balance, and an anatomical positioning system including an electromagnetic field generator for providing three-dimensional positioning of at least one anatomical feature of the patient. The method also includes obtaining a sagittal view radiographic image of a patient's spine using the radiographic system. The method also includes obtaining a frontal view radiographic image of a patient's spine using the radiographic system. Simultaneously with obtaining the sagittal and frontal view radiographic images, the method includes determining a patient's center-of-balance using the balance system. Simultaneously with obtaining the sagittal and frontal view radiographic images, the method also includes monitoring the three-dimensional positioning of one or more anatomical features of the patient.

In another aspect, the present disclosure provides a method of obtaining patient data. The method includes obtaining a radiographic image of at least a portion of a patient's skeletal structure. The method also includes obtaining balance data related to a patient's center-of-balance. Simultaneous with obtaining the balance data, the method includes obtaining position data for at least one anatomical feature of the patient by monitoring the three-dimensional position of the anatomical feature. The method also includes combining the balance data and the patient anatomical position data with the radiographic image data.

Further aspects, forms, embodiments, objects, features, benefits, and advantages of the present invention shall become apparent from the detailed drawings and descriptions provided herein.

BRIEF DESCRIPTION OF THE DRAWINGS

FIG. 1 is a schematic view of a patient analysis system according to an embodiment of the present disclosure.

DESCRIPTION OF EXEMPLARY EMBODIMENTS

Figure 3:
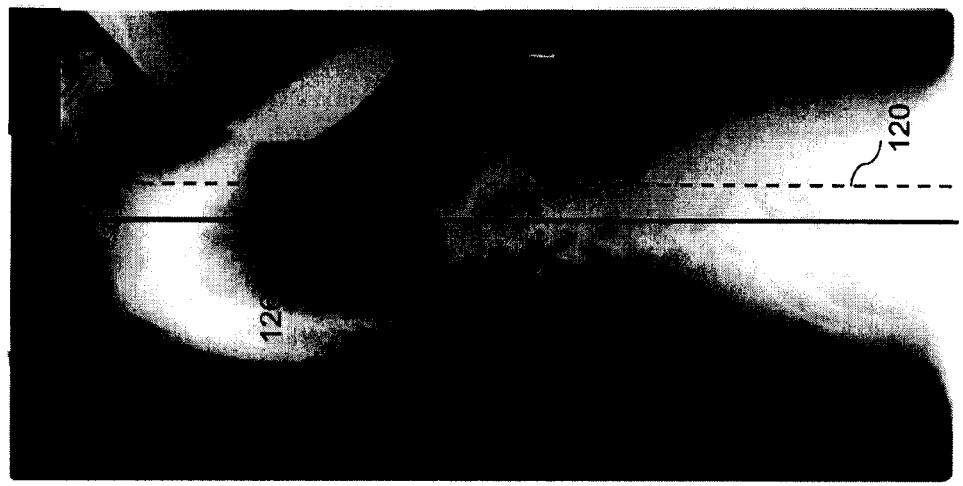
FIG. 3 is a sagittal view radiographic image according to an aspect of the present disclosure.

For the purposes of promoting an understanding of the principles of the present invention, reference will now be made to the embodiments illustrated in the drawings, and specific language will be used to describe the same. It will nevertheless be understood that no limitation of the scope of the invention is intended. In addition, the present disclosure may repeat reference numerals and/or letters in the various exemplary embodiments. This repetition is for the purpose of simplicity and clarity and does not in itself dictate a relationship between the various embodiments and/or configurations discussed. Any alterations and further modifications in the described devices, instruments, methods, and any further application of the principles of the invention as described herein are contemplated as would normally occur to one skilled in the art to which the invention relates.

Referring now to FIG. 1, shown therein is a patient analysis system 100 according to one embodiment of the present disclosure. The patient analysis system 100 includes a radiographic system 102, a balance system 104, and an anatomical positioning system 106. As described in greater detail below, the patient analysis system 100 is capable of combining the patient data provided by the radiographic system 102, the balance system 104, and the anatomical positioning system 106 for use in patient treatment. For example, the patient analysis system 100 may be used for diagnosing and/or categorizing a patient's medical problems, creating a patient treatment plan (e.g., surgical procedures, physical therapy, chemical therapy, and combinations thereof), monitoring the progress of a patient treatment plan, comparing the effectiveness of different treatment plans for patients with similar medical problems, and numerous other medical applications. Further, the patient analysis system 100 may be particularly well suited for use in orthopedic applications. For example, the patient analysis system 100 may be used in the analysis and treatment of spinal disorders. As another example, the patient analysis system 100 may be used in the analysis and treatment of patients likely to receive prosthetic joint replacements (e.g., hip, knee, vertebrae, and ankle). In such embodiments, the patient analysis system 100 may be configured to determine the appropriate prosthetic implant for a patient (e.g., shape, size, design, material, etc.) and monitor the effectiveness of the prosthetic after implantation.

Several additional methods of using the patient analysis system 100 are described in greater detail herein. However, the exemplary methods and uses of the patient analysis system 100 disclosed herein are not to be considered an exhaustive list of the possible uses of the patient analysis system. Rather, the described methods and uses are merely examples of the numerous ways in which the patient analysis system 100 may be utilized. Many other methods of using the patient analysis system 100 will be apparent to one skilled in the art based on the present disclosure.

Figure 2:
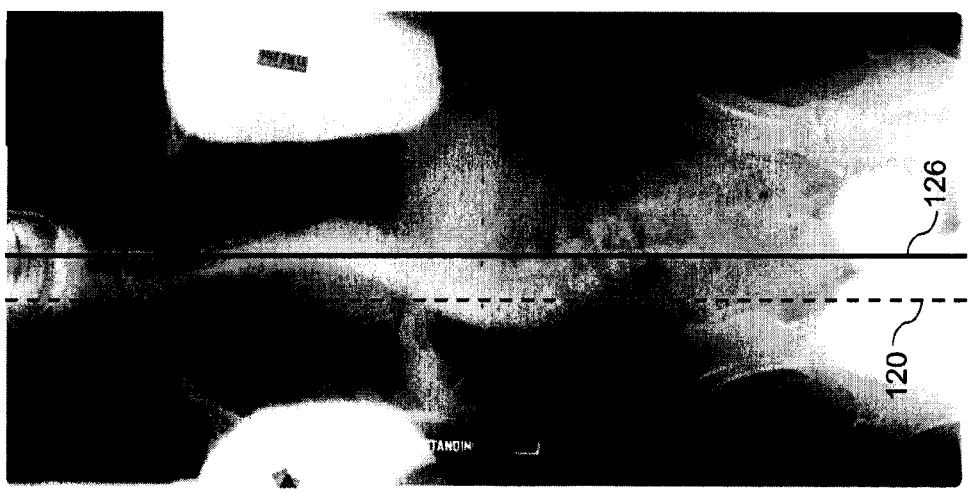
FIG. 2 is a frontal view radiographic image according to an aspect of the present disclosure.

The radiographic system 102 of the patient analysis system 100 is adapted to provide radiographic images of at least a portion of the patient's skeletal structure. In some embodiments, the radiographic system 102 is adapted to provide a radiographic image of the patient's spinal column, pelvis, iliac crest, sacrum, hips, shoulders, and/or clavicles. In other embodiments, the radiographic system 102 is adapted to provide a radiographic image of the patient's spinal column, pelvis, iliac crest, sacrum, hips, shoulders, clavicles, skull, arms, legs, knees, ankles, and/or feet. In other embodiments, the radiographic system 102 is adapted to provide a radiographic image of substantially all of the patient's skeletal structures. The radiographic image of the patient's skeletal structure may be obtained with a single radiographic image or multiple radiographic images. Referring to FIGS. 2 and 3, shown therein are exemplary radiographic images 108 and 110, respectively. The radiographic image 108 of FIG. 2 is a frontal view of the patient's skeletal structure. The radiographic image 110 of FIG. 3 is a sagittal view of the patient's skeletal structure. Further reference will be made to FIGS. 2 and 3 and the radiographic images 108 and 110 below.

Generally speaking, the radiographic system 102 may include x-ray machines, fluoroscopy machines, and/or CT systems. X-ray machines may be utilized to obtain snap-shot images of the patient's skeletal structure. Fluoroscopy machines may be utilized to obtain real-time images of the patient's skeletal structure. In some embodiments, the radiographic system 102 is an existing radiographic system of a medical facility. For example, in many instances the radiographic suite of a medical facility will have a permanently installed x-ray machine. Such x-ray machines and radiographic suites may be used as the radiographic system 102 of the patient analysis system 100.

In some embodiments, the radiographic system 102 is configured to obtain at least sagittal and frontal radiographic images of the patient's anatomy. In some embodiments, the patient simply turns to obtain the desired perspective view for the radiograph. In that regard, the patient may be asked to physically turn herself or himself or, in some embodiments, a moveable platform (see FIG. 5) can rotate the patient between the desired positions such that the patient can remain substantially stationary between positions. In some embodiments the radiographic system 102 is configured to simultaneously obtain sagittal and frontal radiographic images of the patient's anatomy. In addition to the sagittal and frontal views, the radiographic system 102 may be configured to obtain any other views of the patient's anatomy that would be advantageous to patient analysis. Further, the radiographic system 102 may include a radiopaque bead array plate (see FIG. 5). In some embodiments, the radiopaque bead array plate is a plate made substantially of a radiolucent material, but containing a plurality of radiopaque beads. The radiopaque bead array plate and, in particular, the radiopaque beads can serve as a reference point or marker in the resulting radiographic images to orient the features of the patient's skeletal structure to the center of gravity information and the patient anatomical position data. Using the bead array as a reference point, the data obtained from the balance system 104 and the anatomical positioning system 106 may be more accurately combined with the radiographic images within the same coordinate system.

Referring again to FIG. 1, the balance system 104 of the patient analysis system 100 is adapted to provide center-of-balance data for the patient. In that regard, center-of-balance is intended to include information regarding a patient's center-of-gravity, center-of-pressure, center-of-force, and other relevant data regarding the patient's balance. In this regard, the terms center-of-balance, center-of-gravity, center-of-pressure, and center-of-force may be used interchangeably to refer broadly to any data regarding the patient's balance. In some embodiments, the balance system 104 is adapted to provide center-of-balance information for different portions of the patient's anatomy in lieu of or in addition to the overall center-of-gravity of the patient. For example, the balance system 104 may group center-of-balance information based on the left and right sides of the body, vertical anatomical groupings (e.g., ankles and knees, hips and pelvis, spinal column regions, or any other beneficial groupings), any other suitable breakdown of center-of-balance information, and combinations thereof.

In some embodiments, the balance system 104 includes a force and/or pressure sensing pad (see FIG. 5) and a processor for determining the patient's center-of-balance based on the data obtained from the pad. Suitable balance systems including pressure sensing pads are available from TekScan, Inc. located at 307 West First Street, South Boston, Mass. 02127-1309, USA. Other suitable balance systems may be available from other companies.

With respect to the processor of the balance system 104, it is contemplated that the patient analysis system 100 may include a computer system. The computer system may be in communication with one or more of the radiographic system 102, the balance system, and the anatomical positioning system 106. The computer system may be utilized to perform calculations for each of the systems 102, 104, and 106 individually as well as to combine the resultant data from each of the systems 102, 104, and 106. In that regard, the computer system may combine visual data from each of the systems 102, 104, and 106 into a composite visual image for use in the patient's treatment analysis. U.S. patent application Ser. No. 10/169,783, filed Jan. 10, 2001, herein incorporated by reference in its entirety, describes exemplary methods of combining center-of-gravity data with x-ray images. Further, U.S. application Ser. No. 10/877,114, filed Jun. 25, 2004, herein incorporated by reference in its entirety, also describes methods of combining center-of-gravity data with x-ray images. With respect to the embodiments of the patient analysis system 100 that include a computer system, at least some of the functions and calculations of the computer system will be described subsequently herein.

Computer system is understood to refer generally to any device capable of performing the desired functions and calculations required by the patient analysis system 100. A computer system typically includes at least hardware capable of executing machine readable instructions, as well as the software for executing acts (typically machine-readable instructions) that produce a desired result. In addition, a computer system may include hybrids of hardware and software, as well as computer sub-systems. Hardware generally includes at least processor-capable platforms, such as client-machines (also known as personal computers or servers), and hand-held processing devices (such as smart phones, cell phones, personal digital assistants (PDAs), hand-held writing tablets, or personal computing devices (PCDs)). Further, hardware may include any physical device that is capable of storing machine-readable instructions, such as memory or other data storage devices. Other forms of hardware include hardware sub-systems, including transfer devices such as modems, modem cards, ports, and port cards, for example.

Software includes any machine code stored in any memory medium, such as RAM or ROM, and machine code stored on other devices (such as floppy disks, flash memory, or a CD ROM, for example). Software may include source or object code, for example. In addition, software encompasses any set of instructions capable of being executed on a computer system. It is recognized that combinations of software and hardware could also be used for providing enhanced functionality and performance for certain embodiments of the present disclosure. Accordingly, it should be understood that combinations of hardware and software are also included within the definition of a computer system and are envisioned by the present disclosure as possible equivalent structures and equivalent methods.

Figure 4:
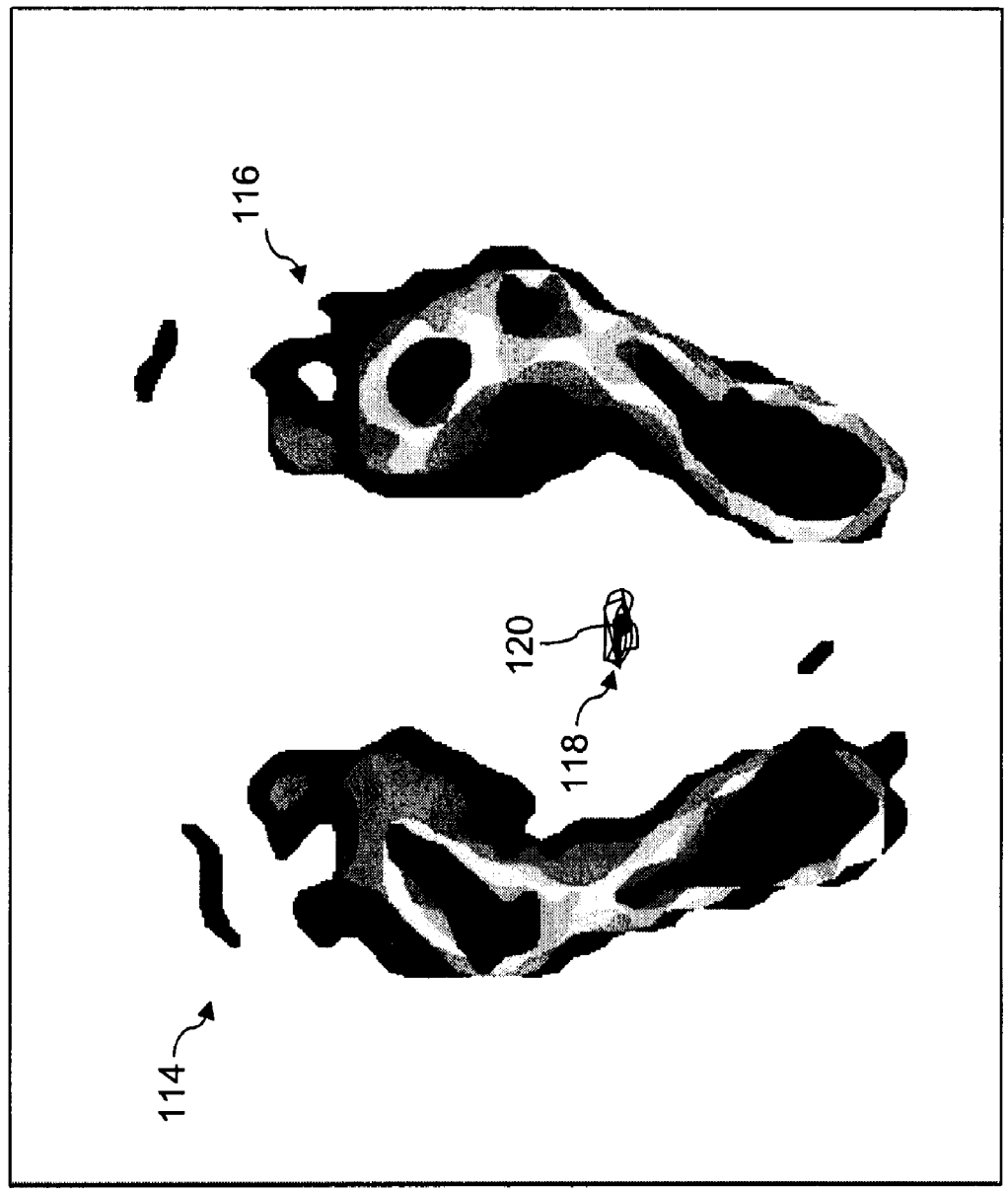
FIG. 4 is a readout from a balance system according to an embodiment of the present disclosure.

Referring now to FIG. 4, shown therein is a readout 112 from the balance system 104 according to one embodiment of the present disclosure. In general, the readout 112 shows the amount of force or pressure on the sensing pad at any given point. The readout 112 of FIG. 4 shows the resultant pressure measurements of a patient standing on the pad. As shown, the readout 112 includes a set of measurements 114 for the left foot of the patient and a set of measurements 116 for the right foot of the patient. Based on the pressure measurements of the left and right feet of the patient, the balance system 104 can determine an overall center-of-gravity for the patient. The center-of-gravity for the patient may be calculated by a computer system in communication with the pad. Typically the patient's center-of-gravity will not be a fixed point, but will vary slightly within a range of positions over a measured time interval. Thus, in some embodiments the overall center-of-gravity for the patient can monitored over a period of time. The balance system 104 can, in turn, utilize the range of center-of-gravity positions and/or calculate an average center-of-gravity for the patient over the measured time frame.

For example, as shown in the readout 112, a center-of-gravity trail 118 represents the instantaneous center-of-gravity for the patient over a predetermined amount of time. An axis 120 extending perpendicular to the pad represents the average center-of-gravity for the patient based on the center-of-gravity trail 118. The axis 120 representing the average center-of-gravity for the patient can then be mapped onto or otherwise combined with the radiographic images 108 and 110, as shown in FIGS. 2 and 3. For example, based on the coordinate system an ideal center-of-gravity for the patient can be determined and then compared to the actual center-of-gravity for the patient. The pressure pad utilizes a set coordinate system that recognized by the underlying software interface. This coordinate system may be used as a reference for combining the data of the balance system 104 with the data from the radiographic system 102 and the anatomical positioning system 106. The coordinate system may be oriented about an anatomical feature(s) of the patient and/or defined by the layout of the force sensing pad. Various reference axis can be used in the data analysis including referencing the coronal plane, sagittal plane, or a horizontal axis along the heels. These axis may or may not be displayed in the view 112.

Referring again to FIG. 1, the anatomical positioning system 106 of the patient analysis system 100 is adapted to provide three-dimensional positional data of an anatomical structure of the patient. In that regard, the anatomical positioning system 106 may include an electromagnetic system, an infrared system, and/or a video system for determining the 3-D position of an anatomical structure. In that regard, the anatomical positioning system 106 may directly detect the position of an anatomical structure and/or detect the position of a sensor in close proximity to the anatomical structure and correlate the position of the anatomical structure to the position of the sensor. Where the anatomical positioning system 106 utilizes a sensor, a plurality of sensors may be utilized. The sensors may be placed on the skin of the patient adjacent the anatomical feature(s) of interest and/or placed on clothing of the patient adjacent the anatomical feature(s). In some embodiments, the sensors are implantable. Implantable sensors may facilitate direct contact with the anatomical feature (s) of interest. Further, implantable sensors may facilitate the accurate detection of the position of internal anatomical features that cannot be accurately determined with external sensors alone. In that regard, sensors may be used both inside and outside of the patient's body. In some embodiments, systems and methods may be used as described in U.S. patent application Ser. No. 10/985,108 filed Nov. 10, 2004, herein incorporated by reference in its entirety.

The 3-D position of numerous anatomical features may be determined with the anatomical positioning system 106. For example, in some embodiments the anatomical positioning system 106 is configured for identifying the location of one or more of the following anatomical features or parts thereof: heels, ankles, knees, hips, iliac crests, sacrum, pelvis, spinal column, spinal column regions, vertebrae, transverse processes, spinal processes, clavicles, and other anatomical features. The actual anatomical features that are located may be depend on numerous factors including physician preference, patient condition, treatment plans, surgical procedures, and other factors. In some embodiments, the anatomical feature(s) of interest may be selected by the treating physician or technician.

In at least one embodiment, the anatomical positioning system 106 utilizes an electromagnetic measurement system to determine the position of the anatomical feature(s) of the patient. Suitable electromagnetic measurement systems are available from Northern Digital, Inc. located at 103 Randall Drive Waterloo, ON N2V 1C5 Canada. Other suitable electromagnetic measurement systems may be available from other companies.

In some embodiments, the electromagnetic measurement system detects the presence of sensors excitable by an electromagnetic field to determine the position of the anatomical features. As described above, the sensors may be external or implantable. The electromagnetic measurement system may utilize a computer system to calculate the 3-D position of the anatomical feature(s) based on the position of the sensors. An advantage of the electromagnetic measurement system is that it does not need to have a line-of-sight with the patient to function properly. Rather, the electromagnetic measurement system can be placed behind and/or underneath other components of the patient analysis system 100 and still function properly. For example, an electromagnetic field generator may be positioned underneath a force sensing pad as described above with respect to the balance system 104 and still function properly by detecting the location of the sensors.

In some embodiments, the electromagnetic measurement system is configured to detect the position of sensors in a fixed volume of space. In that regard, in some embodiments the fixed volume of the electromagnetic measurement system is sufficient to obtain the position of all relevant anatomical features of a patient. In other embodiments, however, the fixed volume may be sufficient to obtain 3-D positions of only some anatomical features of a patient. Where the fixed volume is sufficient to obtain 3-D positions of some, but not all of the patient's anatomical features, a portion of the electromagnetic measure system (e.g., the electromagnetic field generator) may be moveable such that the 3-D positions of the anatomical features of most interest can be obtained. Based on the positions of the anatomical features, the patient analysis system 100 may determine a desired or ideal center-of-balance for the patient and can compare that center-of-balance before and after a surgical or non-surgical treatment. In this regard, the ideal center-of-balance may be based on the orientation of anatomical features to one another, the patient's medical condition, treatment plans, physician preferences, and combinations thereof. In that regard, the ideal center-of-balance for a patient may be a current ideal center-of-balance and not an ultimate ideal center-of-balance. That is, the ideal center-of-balance for the patient may be modified over time as the patient's medical condition changes. After determination of the patient's ideal center-of-balance, an axis 126 representing the patient's ideal center-of-balance can be mapped onto or otherwise combined with the radiographic images 108 and 110, as shown in FIGS. 2 and 3.

In lieu of or in addition to the electromagnetic measurement system, the anatomical positioning system 106 may include an infrared system and/or a video system for determining the 3-D position of the patient's anatomical features. Again, the infrared and/or video systems may utilize sensors to determine the positioning of the patient's anatomical features. In general, infrared and video systems require a direct line-of-sight to the patient and/or sensors. The video system may be a single camera or multi-camera system. In that regard, a multi-camera video system may take the resulting video triangulate the positions of anatomical features of interest using a computer system. Video system in this context is understood to include still photography in addition to moving video.

Figure 5:
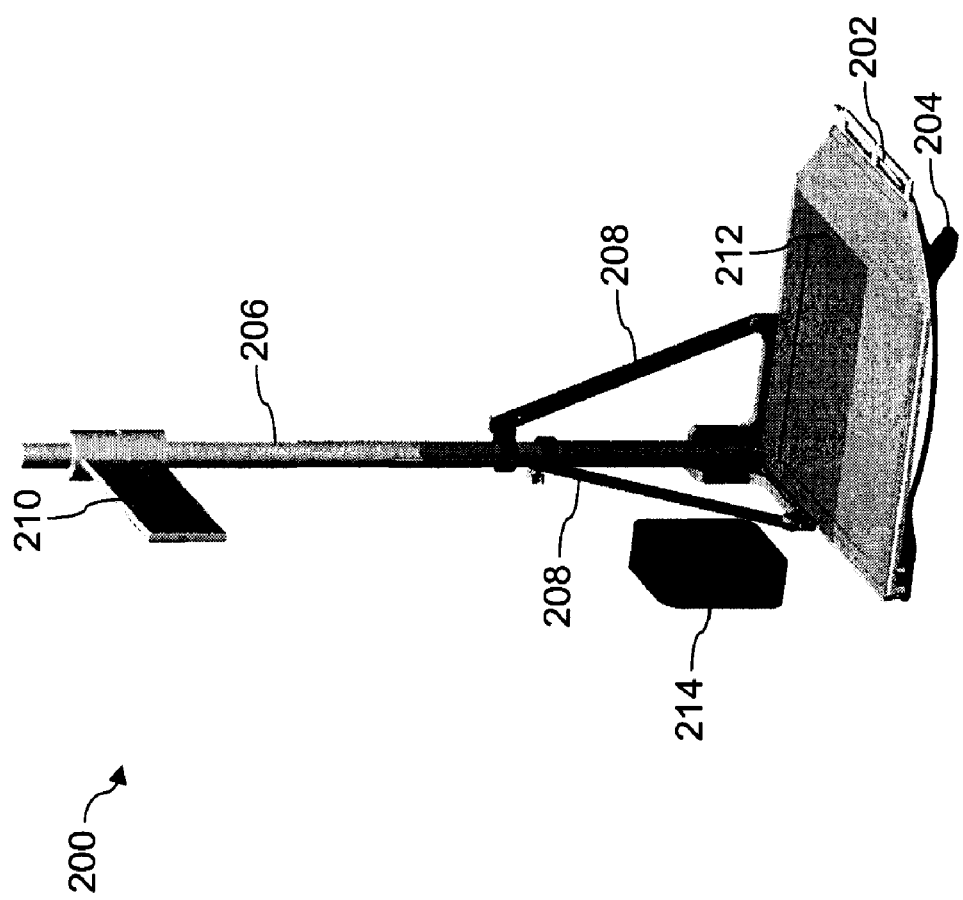
FIG. 5 is a perspective view of some of the components of a patient analysis system according to an embodiment of the present disclosure.

Referring now to FIG. 5, shown therein are some of the components of a patient analysis system 200 according to one embodiment of the present disclosure. The patient analysis system 200 may be substantially similar to the patient analysis system 100. In that regard, the patient analysis system 200 may incorporate aspects of the radiographic system 102, the balance system 104, and the anatomical positioning system 106 described above. The patient analysis system 200 includes a platform 202 for supporting a patient. In that regard, in some embodiments the platform 202 is formed of a metal or hard plastic of sufficient thickness to support the weight of a patient. In at least one embodiment, the platform 202 is formed of titanium with a thickness of approximately ½ inch. In some embodiments, the platform 202 is substantially planar. The platform 202 is connected to a base 204. The base 204 is stationary and adapted to maintain contact with the floor or other surface on which the patient analysis system is placed. In some embodiments, the platform 202 is raised several inches from the floor. In other embodiments, the platform 202 may be positioned substantially on the floor. In some embodiments, the platform 202 may be leveled. In that regard, the platform 202 may be leveled via a manual and/or an automatic system to ensure that the platform is level.

In some embodiments, the platform 202 is rotatably connected to the base 204 such that the platform can rotate about the base. In that regard, in some embodiments, the platform 202 is particularly adapted to rotate between a first position for obtaining a radiograph of the patient from a first view (e.g., frontal) and a second position for obtaining a radiograph of the patient from a second view (e.g., sagittal). The patient analysis system 200 may include additional features to facilitate the rotation of the platform 202, such as wheels, bearings, motors, or other devices. In some embodiments, the platform 202 may be rotated manually. In some embodiments, the platform 202 may be rotated by a motor or other powered mechanism. The platform 202 may be limited to approximately 90 degrees of rotation in some embodiments. In other embodiments, the platform 202 may be allowed to rotate more or less. In some embodiments, the platform is configured to facilitate obtaining oblique views of the patient. In that regard, in some embodiments oblique views may be used to resolve complex deformity analysis. In some embodiments, the platform 202 is substantially stationary and does not rotate about the base 204. In some embodiments, the pressure pad itself can serve as the platform 202 and reside directly on the floor.

The patient analysis system 200 also includes an elongated post or shaft 206. The post 206 is connected to the platform 202 via braces 208. In the current embodiment, the post 206 is substantially perpendicular to the plane defined by the platform 202. In some embodiments, the three-dimensional coordinate system defined by the plane of the platform 202 and the bead array 210 can be utilized to help integrate the data obtained from each of the radiographic, balance, and anatomical positioning systems. In that regard, the intersection point between the post 206 and the platform 202 may serve as an origin. In that regard, the data from each of the systems can be correlated to the origin and then combined based on this common coordinate system. The actual integration of the data and correlation of each of the systems measurements to the coordinate system defined by the platform 202 and the bead array 210 may be performed by a computer system. In some embodiments, sensors attached to and/or implanted into the patient's body can be used as reference points to define a coordinate system.

In some embodiments, the post 206 is substantially fixed with respect to the platform 202. In such embodiments, the platform 202 and the post 206 may rotate about the base 204. Alternatively, in such embodiments the platform 202 and the post 206 may be substantially stationary. In some embodiments, the post 206 is retractable. That is, the post 206 may collapse to a shorter length and/or be comprised of multiple pieces that can be assembled together to form the full post. A collapsible or multiple component post may be advantageous in portable embodiments of the patient analysis system 200.

The patient analysis system 200 also includes components described above with respect to the radiographic system 102, the balance system 104, and the anatomical positioning system 106. For example, a plate 210 is movably connected to the post 206. The plate 210 may include a radiopaque bead array for providing orientation/positioning data to the radiographic images of the patient's skeletal structure. In that regard, the plate 210 may provide a coordinate system for the radiographic images. The plate 210 may be moved along the post 206 for placement within the range of the radiographic image. In that regard, in embodiments where the radiographic images are to be taken of the patient's spine, the plate 210 may positioned within the stomach or chest region of the patient. In embodiments where radiographic images are to be taken of other portions of the patient's skeletal system, the plate 210 may be positioned accordingly.

The patient analysis system 200 also includes a pressure sensing pad 212 positioned on the support platform 202. In some embodiments, the pressure sensing pad 212 and the platform 202 are permanently attached or integrally formed with one another. In other embodiments, the pressure sensing pad 212 is selectively attached to the platform 202. The platform 202 and/or the pad 212 may include features to facilitate proper alignment between the platform and the pad. For example, the platform 202 may include a recess configured to receive a projection of the pad 212 and/or the pad may include a recess configured to receive a projection of the platform. The pad 212 may also be used without the platform 202.

The patient analysis system 200 also includes a component 214 of the anatomical positioning system. In the current embodiment, the component 214 is an electromagnetic field generator. As shown, the electromagnetic field generator is positioned adjacent the platform 202 and the sensing pad 212. In some embodiments the electromagnetic filed generator is positioned underneath the platform 202 and the sensing pad 212. In that regard, in some embodiments, the platform 202 may include an opening or other feature adapted to receive at least a portion of the electromagnetic field generator and secure it in place. In yet other embodiments, the electromagnetic field generator may be connected to the post 206 and/or the supports 208. In that regard, in some embodiments the electromagnetic field generator is slidably connected to the post 206 so that it may be moved along the post to a desired position. In other embodiments, the component 214 is part of an infrared or video system. In such embodiments, the component 214 should be positioned within a direct line-of-sight to the volume directly above the pad 212.

The patient analysis systems 100 and 200 described above and similar systems are capable of combining the patient data provided by a radiographic system, a balance system, and a anatomical positioning system for use in patient treatment. For example, the patient analysis systems may be used for diagnosing and/or categorizing a patient's medical problems, creating a patient treatment plan (e.g., surgical procedures, physical therapy, chemical therapy, and combinations thereof), monitoring the progress of a patient treatment plan, comparing the effectiveness of different treatment plans, and numerous other medical applications. Further, the patient analysis systems may be particularly well suited for use in orthopedic applications, including the treatment of spinal disorders and prosthetic joint replacements, including intervertebral body disc replacements. Several exemplary methods of using the patient analysis systems will now be described. However, these exemplary methods are not to be considered an exhaustive list of the possible uses of the patient analysis system, but rather illustrate the types of ways in which the patient analysis systems may be utilized. Many other methods of using the patient analysis systems may be apparent to one skilled in the art based on the methods described below.

Figure 6:
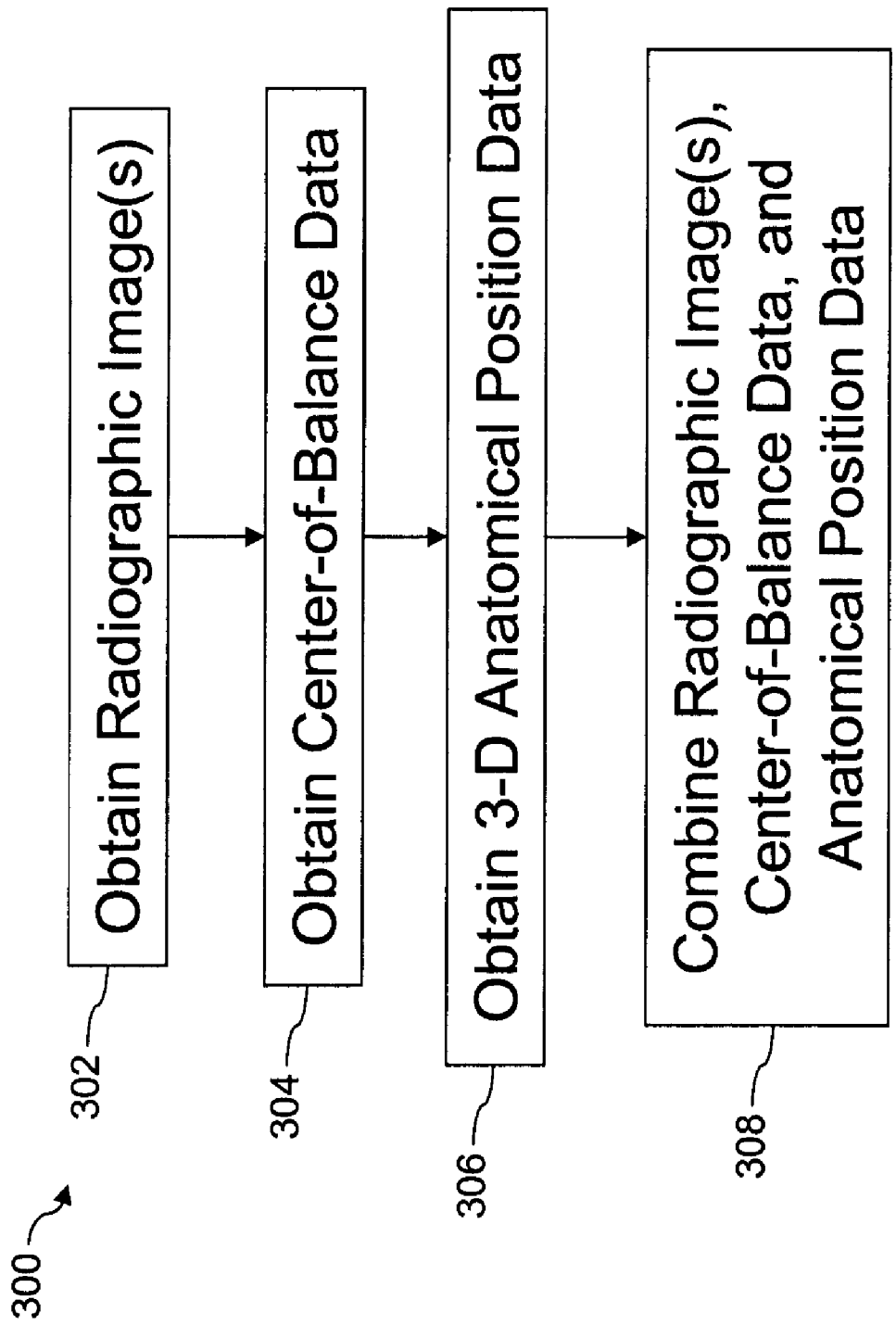
FIG. 6 is a flowchart representative of a method according to an embodiment of the present disclosure.

Referring now to FIG. 6, shown therein is a flowchart representing a method 300 according to one embodiment of the present disclosure. The method 300 begins at step 302 with obtaining a radiographic image or images of a patient. The anatomy captured in the radiographic images and the perspective view (e.g., frontal, sagittal, axial, oblique, and combinations thereof) of the radiographic images may be determined by a treating physician or technician and/or a computer system based on the patient's perceived medical problems. In some embodiments, the radiographic image will be taken of the patient's spinal column, pelvis, sacrum, hips, shoulders, and/or clavicles. In other embodiments, the radiographic image will be taken of the patient's spinal column, pelvis, sacrum, iliac crests, hips, shoulders, clavicles, skull, arms, legs, knees, ankles, and/or feet. In other embodiments, the radiographic image will be taken of substantially all of the patient's skeletal structures. The radiographic image of the patient's skeletal structure and parts thereof may be obtained with a single radiographic image or multiple radiographic images. Often the radiographic images will be taken in the frontal and/or sagittal views. However, in other instances the radiographic images may be taken from a frontal view, sagittal view, an axial view, an oblique view, and/or combinations thereof.

The method 300 continues at step 304 with obtaining center-of-balance data for the patient. In some embodiments, the center-of-balance data is obtained using a force sensing pad and processing as described above with respect to patient analysis systems 100 and 200. In some embodiments, the center-of-balance data may be obtained simultaneously with the radiographs of step 302. In that regard, the balance system and the radiographic system may be integrated into a single system or may be in communication with a common interface (e.g., laptop computer or shared trigger mechanism) such that the center-of-balance data and the radiographic images are obtained simultaneously. In some embodiments, the balance system and the radiographic system are completely separate. However, the center-of-balance data may still be obtained simultaneously with the radiographs. For example, a technician may simply trigger the two systems at substantially the same time by activating one system with one hand the other system with the other hand. Similarly, in embodiments where the center-of-balance data may be obtained over an extended time period (e.g., 30 seconds or more) the radiographic images may be taken during this time period. The timing of the radiographic images can be noted and correlated to the instantaneous center-of-balance data for that time. In other embodiments, the center-of-balance data is not obtained simultaneously with the radiographs.

The method 300 continues at step 306 with obtaining 3-D anatomical positioning data for a portion of the patient's anatomy. In some embodiments, the 3-D position data is obtained using an electromagnetic measurement system, an infrared system, and/or a video system as described above with respect to patient analysis systems 100 and 200. In some embodiments, the 3-D position data may be obtained simultaneously with the radiographs of step 302 and/or the center-of-balance data of step 304. In that regard, the 3-D positioning system, the balance system, and/or the radiographic system may be integrated into a single system or may be in communication with a common interface (e.g., laptop computer or shared trigger mechanism) such that the 3-D position data, the center-of-balance data, and/or the radiographic images are obtained simultaneously.

In particular, in some embodiments the 3-D positioning system and the balance system are in communication with a common computer system. In this manner, real-time data for 3-D position and center-of-balance may be correlated to one another by the computer system or other common interface. That is, the 3-D position data at a certain time and the center-of-balance data at that same time can be grouped together, so that both the 3-D position data and the center-of-balance data for that instant in time are known. In addition, the data may be correlated over longer time periods as well.

The portion of the patient's anatomy for which 3-D positional data is obtained may be determined by a treating physician or technician, a computer system based on the patient's perceived medical problems, and/or based on the anatomy captured by the radiographs in step 302. In that regard, the positions of one or more of the following anatomical features or parts thereof may be identified: heels, ankles, knees, hips, iliac crests, sacrum, pelvis, vertebrae, clavicles, and other anatomical features.

In that regard, the 3-D positional data may be determined by the location of the actual anatomical structure of the patient and/or the location of a sensor in close proximity to the anatomical structure of the patient. Where sensors are utilized, a plurality of sensors may be utilized for each pertinent anatomical structure. In some embodiments, the sensors may be placed on the skin of the patient adjacent the anatomical features of interest and/or placed on clothing of the patient adjacent the anatomical features. In some embodiments, the sensors are implantable. In such embodiments, an implantable sensor may be placed in direct contact with or substantially close to the anatomical features of interest. Implantable sensors may be used to facilitate more accurate detection of the position of internal anatomical features than possible with external sensors alone. In that regard, in some embodiments sensors may be used both inside and outside of the patient's body for obtaining 3-D positional data.

The method 300 continues at step 308 with combining the radiographic image(s), center-of-balance data, and 3-D anatomical positioning data. In this regard, in some embodiments a computer system is used to combine the data from each of the systems. The terms combine and/or correlate as used herein are intended to convey the concept of using the images and/or data from the systems together. There is no requirement that the images and/or data actually be compiled or merged into a single data object. However, combine and/or correlate certainly includes situations where the images and/or data are compiled or merged together. Combine and/or correlate should be understood broadly to mean using information (e.g., images, data, etc.) from a system together with information from the same system or another system.

In some instances, the images and data are combined to provide a snap-shot of the patient's condition. That is, the center-of-balance data and the 3-D positioning data for the same time that a radiographic image was taken are combined to give an instantaneous look at the patient's condition. Where multiple radiographic images have been taken, combining the data may provide several snapshots of the patient's condition at different moments and from different perspectives. Further, in some instances the images and data are combined to create a database of the patient's condition over a specific time frame. For example, where the radiographic images of the patient are obtained using a fluoroscopy device such that real-time radiographic images of the patient are available over a specific period of time, these radiographic images may be combined with simultaneous real-time data from the balance and positioning systems to create a database of the patient's condition over that period of time. Subsequently, the database may be analyzed and/or instantaneous snapshots of the patient's condition may be retrieved from the time period and analyzed. The images and data may be combined in numerous other ways. The way in which the images and/or data are combined may be determined by the treating physician and/or may be based on the way in which the combined information is to be used. Generally, any type of combination of the images and data from the radiographic system, the balance system, and/or the 3-D positioning system is contemplated as being within the scope of the present disclosure.

The combined images and data may be put to many uses. For example, in some instances a treating physician may be determine an appropriate treatment plan based on the combined information. In that regard, the patient may be categorized based on an analysis of the combined data. A physician may then choose between a group of treatment options found to be effective for patients in that category. Further, the combined data may be utilized in research settings to monitor and/or determine the effectiveness of various treatment methods for patients with similar medical problems. Based on the effectiveness of the various treatment methods for known medical problems, a hierarchy of preferred treatment methods and combinations of treatment methods may be created based on a specific patient's medical condition. In addition to these exemplary uses, the combined data may be used in many other ways within the context of medical applications, including diagnosing, treating, monitoring, researching, characterizing, and otherwise investigating various medical conditions.

Figure 7:
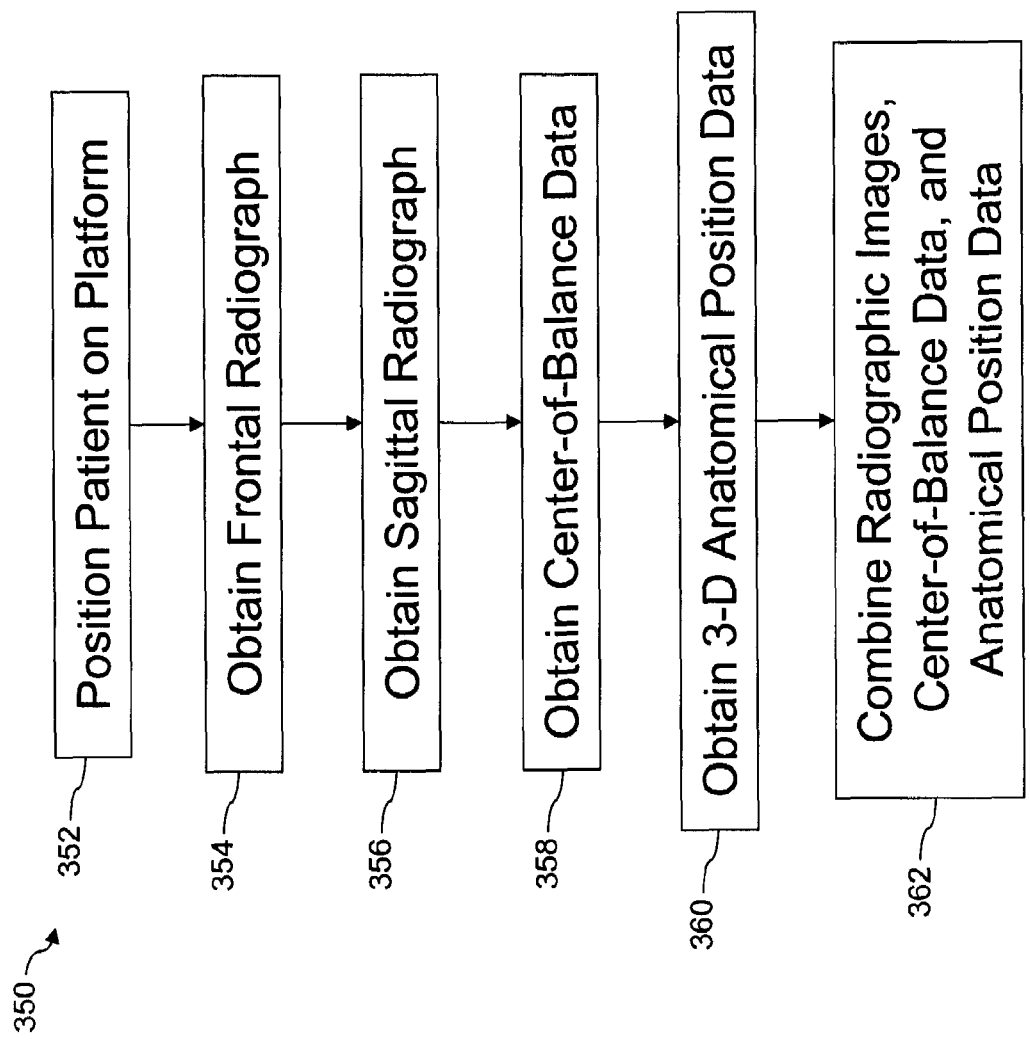
FIG. 7 is a flowchart representative of a method according to an embodiment of the present disclosure.

Referring now to FIG. 7, shown therein is a flowchart representing a method 350 according to one embodiment of the present disclosure. In some aspects the method 350 may be similar to the method 300 described above. For that reason, some of the steps of the method 350 may not be described in great detail. The method 350 begins at step 352 with positioning a patient onto a platform. In some embodiments, the platform is similar to platform 202 described above and may include a pressure sensing pad. In most instances, the patient will stand on the platform. However, in some embodiments the patient may sit or kneel on the platform. The method 350 continues at step 354 with obtaining a frontal radiographic image of the patient. The method 350 continues at step 356 with obtaining a sagittal radiographic image of the patient. The method 350 continues at step 358 with obtaining center-of-balance data for the patient. The method 350 continues at step 360 with obtaining 3-D anatomical positioning data for a portion of the patient's anatomy. The method 350 continues at step 362 with combining the radiographic image(s), center-of-balance data, and 3-D anatomical positioning data.

Figure 8:
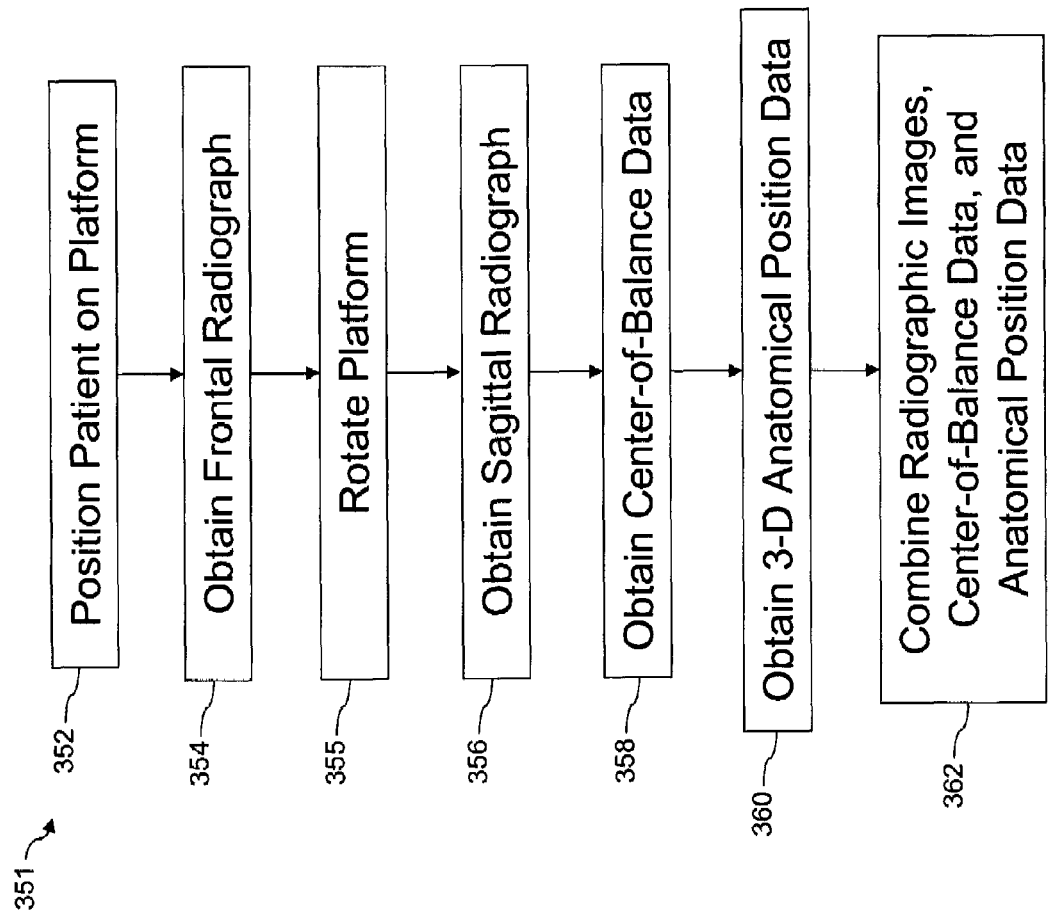
FIG. 8 is a flowchart representative of a method according to an embodiment of the present disclosure.

Referring now to FIG. 8, shown therein is a flowchart representing a method 351 according to one embodiment of the present disclosure. In many aspects the method 351 may be substantially similar to the method 350 described above and, therefore, the majority of the steps of method 351 will not be discussed again in detail. However, the method 351 requires an additional step that is optional in method 350 described above. In particular, the method 351 includes step 355 in which the platform is rotated. The rotation of the platform may assist in positioning the patient for taking of the radiographic images. For example, in at least one embodiment the patient is first positioned on the platform for the frontal radiographic image of step 354. Then, the platform may be rotated to properly align the patient for a sagittal or lateral radiographic image of step 356. In other embodiments, other combinations of radiographic image views, including oblique angles, may be used and the platform may be rotated accordingly to position the patient.

Figure 9:
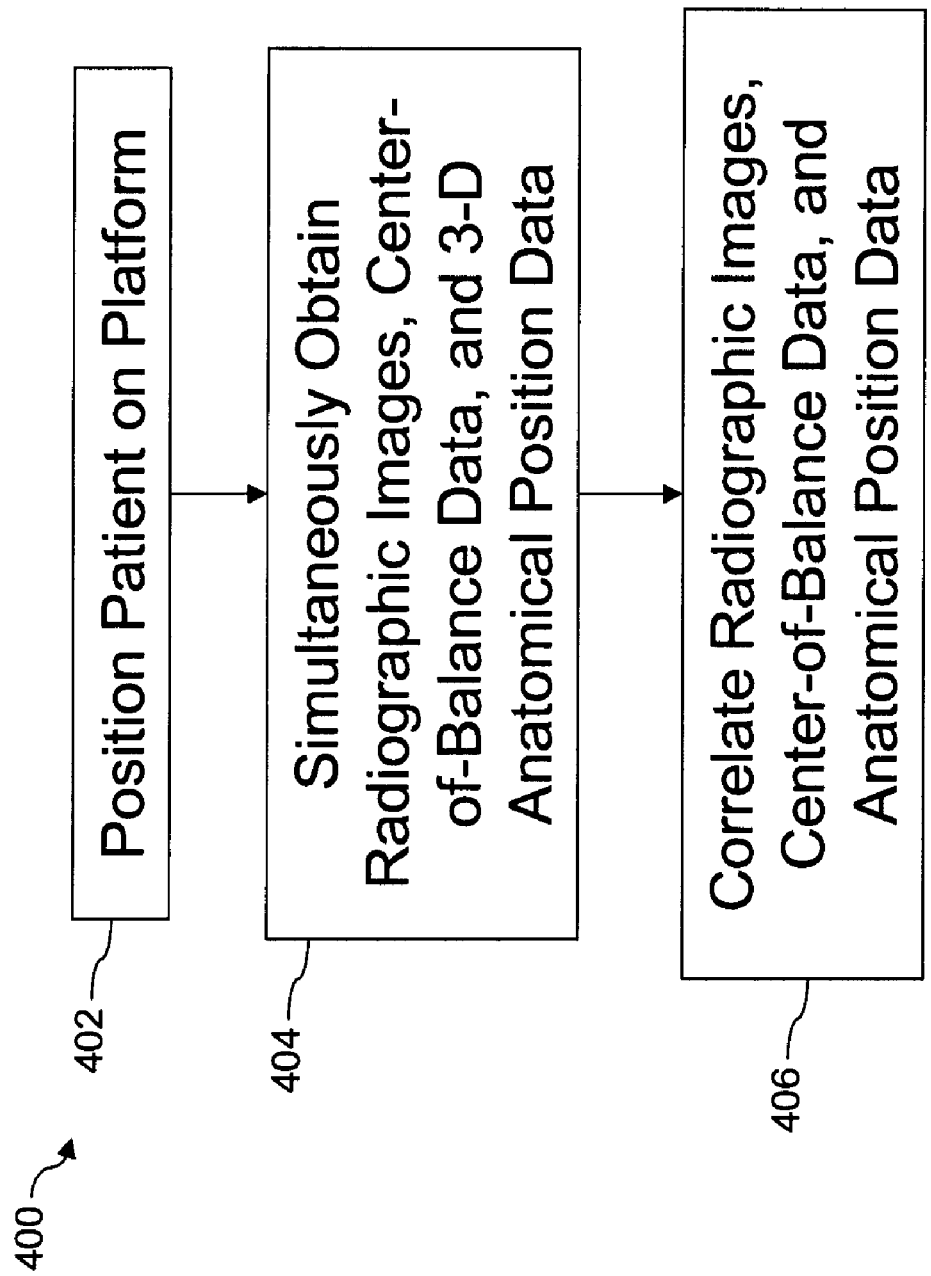
FIG. 9 is a flowchart representative of a method according to an embodiment of the present disclosure.

Referring now to FIG. 9, shown therein is a flowchart representing a method 400 according to one embodiment of the present disclosure. In some aspects, the method 400 may be similar to the methods 300, 350, and 351 described above. For that reason, some of the steps of the method 400 may not be described in great detail. The method 400 begins at step 402 with positioning a patient onto a platform. The method 400 continues at step 404 with simultaneously obtaining radiographic image(s), center-of-balance data, and 3-D anatomical position data for a patient. In this regard, it is contemplated that the center-of-balance data and the 3-D anatomical positioning data may be obtained continuously over a period of time. In some embodiments, the center-of-balance data and the 3-D anatomical positioning data are obtained over a set interval of time, between 5 seconds and 1 minute in some embodiments. The radiographic images may be taken during the period of time in which the center-of-balance data and the 3-D anatomical positioning data are being obtained. The radiographic images may be obtained using an x-ray machine such that the images are snapshots of the patient's skeletal structure. On the other hand, in some embodiments the radiographic images may be obtained by fluoroscopy device such that a continuous stream of real-time radiographic images are available. The fluoroscopy device may be activated during the data acquisition time period of the balance and positioning systems. In some embodiments, the fluoroscopy device is run for the same set interval of time as the balance and positioning systems. The method 400 continues at step 406 with correlating the radiographic image(s), center-of-balance data, and 3-D anatomical positioning data.

Figure 10:
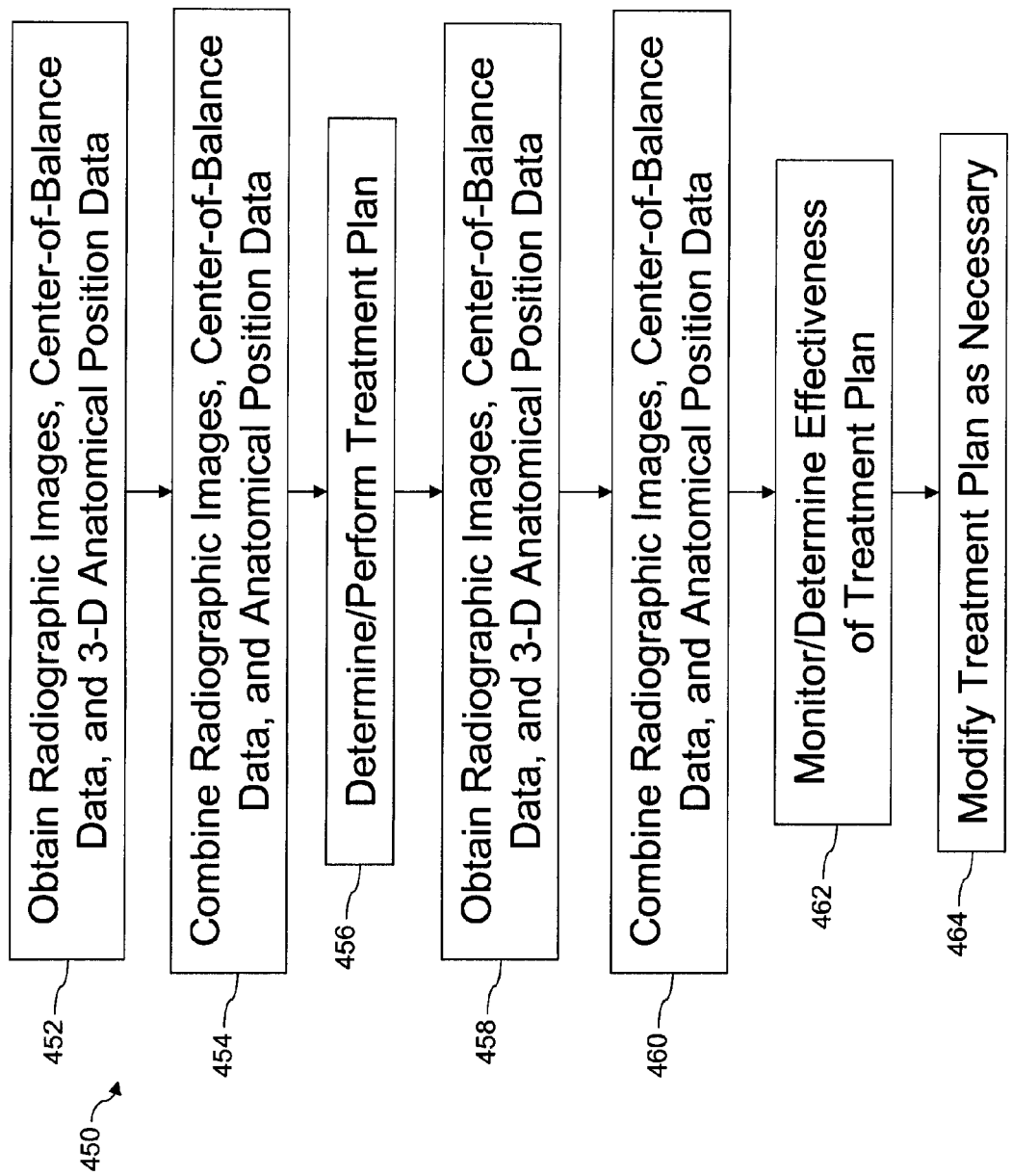
FIG. 10 is a flowchart representative of a method according to an embodiment of the present disclosure.

Referring now to FIG. 10, shown therein is a flowchart representing a method 450 according to one embodiment of the present disclosure. In some aspects, the method 400 may be similar to the methods 300, 350, 351, and 400 described above. For that reason, some of the steps of the method 450 may not be described in great detail. The method 450 begins at step 452 with obtaining radiographic image(s), center-of-balance data, and 3-D anatomical position data for a patient. The method 450 continues at step 454 with combining the radiographic image(s), center-of-balance data, and 3-D anatomical positioning data. The method 450 continues at step 456 with determining and/or performing a treatment plan based on the combined radiographic image(s), center-of-balance data, and 3-D anatomical positioning data. The treatment plan may include surgical procedures, physical therapy, chemical therapy, and combinations thereof. In some embodiments, the treatment plan may be based on a classification of the patient determined from the combined radiographic image(s), center-of-balance data, and 3-D anatomical positioning data.

The method 450 continues at step 458 with obtaining updated radiographic image(s), center-of-balance data, and 3-D anatomical position data for a patient. In general, the updated radiographic image(s), center-of-balance data, and 3-D anatomical position data are obtained after the treatment plan of step 456 has been started. In some embodiments, the updated radiographic image(s), center-of-balance data, and 3-D anatomical position data are obtained after a surgical procedure. In some embodiments, the updated radiographic image(s), center-of-balance data, and 3-D anatomical position data are obtained at a fixed interval of time after the start of the treatment plan. The specific interval of time for a patient may be determined by the treating physician and/or be based on the treatment plan. The method 450 continues at step 460 with combining the updated radiographic image(s), center-of-balance data, and 3-D anatomical positioning data.

The method 450 continues at step 462 with determining the effectiveness of the treatment plan based on the combined updated radiographic image(s), center-of-balance data, and 3-D anatomical positioning data. In this regard, the updated images and data may be compared with the initial images and data. The progress of the patient and/or the effectiveness of the treatment plan may then be determined. In some embodiments, the comparison of the updated and initial data sets is performed by a computer system. In such an embodiment, the effectiveness of a treatment plan can be determined objectively based on predetermined factors. In other embodiments, the comparison is performed by a treating physician or technician.

The method 450 continues at step 464 with modifying the treatment plan, as necessary, based on the combined updated radiographic image(s), center-of-balance data, and 3-D anatomical positioning data. For example, where the treatment plan has not been as effective as hoped or has resulted in additional complications, the treatment plan may be modified accordingly. Further, where the treatment plan has been completely successful, the treatment plan may be modified to move to a next stage or phase of the treatment plan. Generally, the treatment plan may be continued, modified, abandoned, or otherwise changed in response to the updated radiographic image(s), center-of-balance data, and 3-D anatomical positioning data. Appropriate changes to the treatment plan may be suggested either by a computer system or a treating physician.

Figure 11:
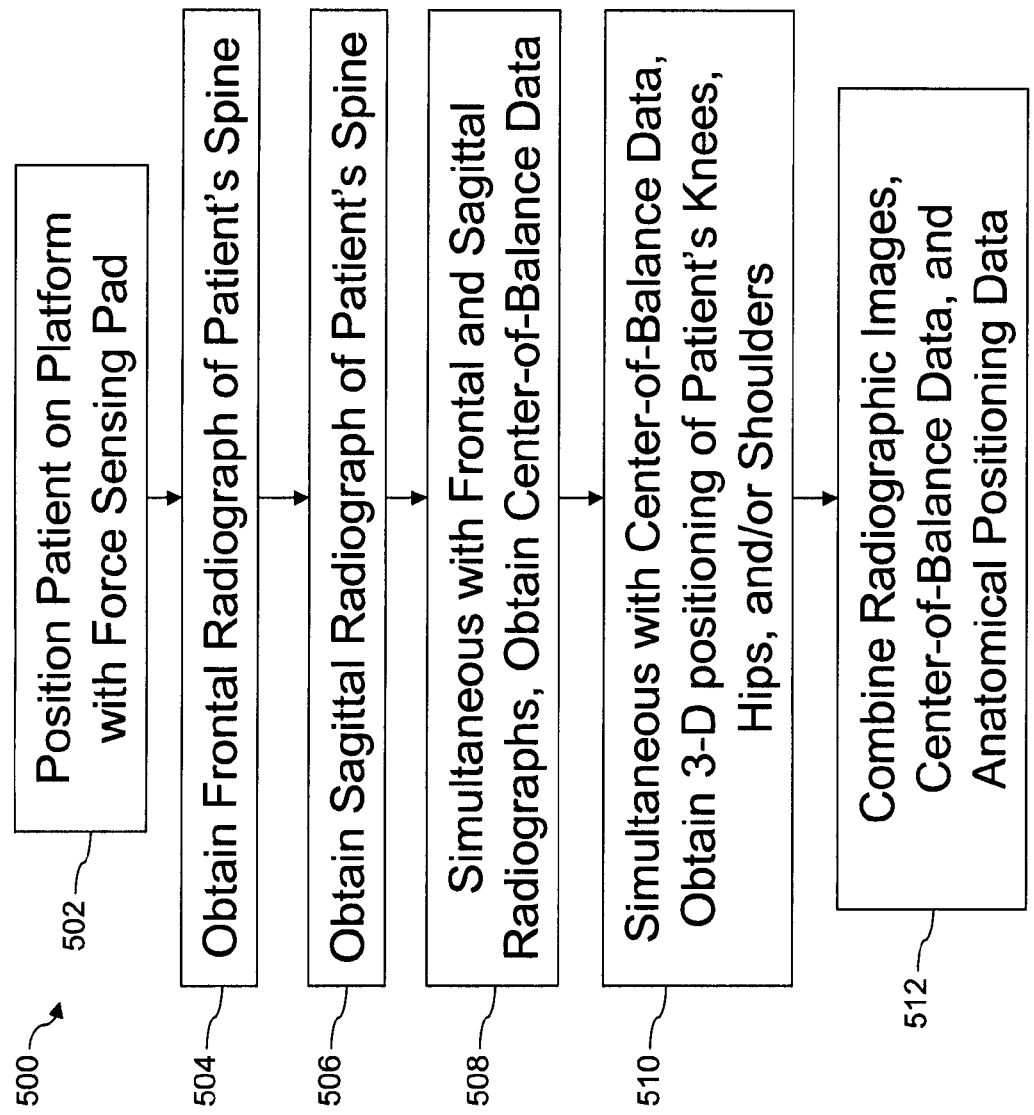
FIG. 11 is a flowchart representative of a method according to an embodiment of the present disclosure.

Referring now to FIG. 11, shown therein is a flowchart representing a method 500 according to one embodiment of the present disclosure. In some aspects, the method 500 may be similar to the methods 300, 350, 351, 400, and 450 described above. For that reason, some of the steps of the method 500 may not be described in great detail. The method 500 begins at step 502 with positioning a patient on platform having a force sensing pad. The method 500 continues at step 504 with obtaining a frontal radiograph of at least a portion of the patient's spine. The method 500 continues at step 506 with obtaining a sagittal radiograph of at least a portion of the patient's spine. The method 500 continues at step 508 with obtaining center-of-balance data for the patient. In some embodiments, the center-of-balance data is obtained simultaneously with the obtaining of the frontal and sagittal radiographs. The method 500 continues at step 510 with obtaining 3-D positioning of the patient's knees, hips, and/or shoulders. Which of these anatomical structures positioning data is obtained for may be based on physician preference and/or the limitations of the positioning system. In some embodiments, the position of the knees is based on the location of the patient's patellas. Similarly, the position of the hips is determined based on the location of the patient's iliac crests. Similarly, in some embodiments the position of the shoulders is determined based on the location of the patient's clavicles. In some embodiments, the 3-D positioning data is obtained simultaneously with the obtaining of the center-of-balance data and, therefore, also simultaneously with the obtaining of the frontal and sagittal radiographs. The method 500 continues at step 512 with combining the frontal and sagittal radiographic images, center-of-balance data, and 3-D anatomical positioning data.

The foregoing outlines features of several exemplary embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A patient analysis system, comprising:
a platform for supporting a patient;
a radiographic system for providing radiographic images of at least a portion of a patient's skeletal structure while the patient stands on the platform;
a balance system for determining a patient's center-of-balance while the patient stands on the platform, wherein the balance system determines the patient's center-of-balance at least partially based on the patient's weight distribution; and
an anatomical positioning system for providing three-dimensional positioning data for at least one of the patient's anatomical structures while the patient stands on the platform;
wherein the at least a portion of the patient's skeletal structure includes a majority of the patient's spinal column;
wherein the radiographic images are selected from the group consisting of frontal and sagittal views; and
wherein the anatomical positioning system utilizes infrared monitoring.

2. A patient analysis system, comprising:
a platform for supporting a patient;
a radiographic system for providing radiographic images of at least a portion of a patient's skeletal structure while the patient stands on the platform;
a balance system for determining a patient's center-of-balance while the patient stands on the platform, wherein the balance system determines the patient's center-of-balance at least partially based on the patient's weight distribution; and
an anatomical positioning system for providing three-dimensional positioning data for at least one of the patient's anatomical structures while the patient stands on the platform;
wherein the at least a portion of the patient's skeletal structure includes a majority of the patient's spinal column;
wherein the radiographic images are selected from the group consisting of frontal and sagittal views; and
wherein the anatomical positioning system includes an electromagnetic field generator.

3. The patient analysis system of claim 2 wherein the at least one of the patient's anatomical structures is selected from the group consisting of the patient's heels, ankles, knees, hips, iliac crests, sacrum, pelvis, vertebrae, and clavicles.

4. The patient analysis system of claim 2 wherein the anatomical positioning system further comprises at least one sensor for placement adjacent to at least one of the patient's anatomical structures.

5. The patient analysis system of claim 4 wherein the at least one sensor is implantable.

6. The patient analysis system of claim 4 wherein the balance system includes a force sensing pad positioned on the platform.

7. The patient analysis system of claim 6, wherein the radiographic system, the balance system, and the anatomical positioning system are operable simultaneously.

8. A patient analysis system, comprising:
an elongated post;
a platform for supporting a patient, the platform rotatably connected to the post;
a radiographic system for providing radiographic images of at least a portion of a patient's skeletal structure while standing on the platform, the radiographic system including at least one bead array movably connected to the post;
a balance system for determining a patient's center-of-balance while standing on the platform, the balance system including a force sensing pad positioned on the platform; and
an anatomical positioning system for providing three-dimensional positioning data for at least one of the patient's anatomical structures while standing on the platform, the anatomical positioning system including an electro-magnetic field generator positioned adjacent the platform.

9. The system of claim 8, wherein the platform can rotate at least 90 degrees.

10. The system of claim 9, wherein the anatomical positioning system provides positioning data for at least one of the patient's anatomical structures selected from the group consisting of the patient's heels, ankles, knees, hips, iliac crests, sacrum, pelvis, vertebrae, and clavicles.

11. The system of claim 10, wherein the anatomical positioning system further comprises at least one sensor for placement adjacent to at least one of the patient's anatomical structures.

12. The system of claim 11, wherein the at least one sensor is implantable.

13. The system of claim 11, wherein the post, the platform, the balance system, and the anatomical positioning system are portable.

14. A portable patient analysis system for use with a radiographic system of a medical facility, comprising:
a platform for supporting a patient;
an elongated post, the post connectable to the platform;
a radiopaque bead array plate connectable to the post;

a balance system for determining a patient's center-of-gravity while standing on the platform, the balance system including a force sensing pad configured for placement on the platform; and an anatomical positioning system for providing three-dimensional positioning data for at least one of the patient's anatomical structures while standing on the platform, the anatomical positioning system including an electro-magnetic field generator configured for placement adjacent the platform;

wherein the electromagnetic field generator is configured for placement under the platform.

15. The system of claim 14, wherein the elongated post is retractable.

16. The system of claim 14, further comprising a computer system for communication with the balance system and the anatomical positioning system.

17. A method of obtaining patient data, comprising:
providing a patient analysis system comprising:
 a radiographic system for providing radiographic images of at least a portion of a patient's skeletal structure;
 a balance system including a force sensing pad for determining a patient's center-of-balance; and
 an anatomical positioning system including an electromagnetic field generator for providing three-dimensional positioning of at least one anatomical feature of the patient;
obtaining a sagittal view radiographic image of a patient's spine using the radiographic system;
obtaining a frontal view radiographic image of a patient's spine using the radiographic system;
simultaneously with obtaining the sagittal and frontal view radiographic images determining a patient's center-of-balance using the balance system; and
simultaneously with obtaining the sagittal and frontal view radiographic images monitoring the three-dimensional positioning of at least one anatomical feature of the patient.

18. The method of claim 17, wherein the obtaining the sagittal and frontal view radiographic images are performed simultaneously.

19. The method of claim 17, wherein the monitoring the three-dimensional positioning of the patient's anatomical structure includes monitoring the position of a sensor placed in proximity to the patient's anatomical structure.

20. The method of claim 19, wherein the at least one anatomical feature of the patient is selected from the group consisting of the patient's knees, iliac crests, and clavicles.

21. The method of claim 19, wherein the at least one anatomical feature of the patient is selected from the group consisting of the patient's heels, ankles, knees, hips, iliac crests, sacrum, pelvis, vertebrae, and clavicles.

22. A method of obtaining patient data, comprising:
obtaining a radiographic image of at least a portion of a patient's skeletal structure;
obtaining balance data related to a patient's center-of-balance;
simultaneous with obtaining the balance data, obtaining position data for at least one anatomical feature of the patient by monitoring the three-dimensional position of the at least one anatomical feature; and
combining the balance data and the position data with the radiographic image;
wherein the obtaining the radiographic image, the obtaining balance data, and the obtaining position data are synchronized to facilitate 3-D reconstruction of at least a portion of the patient's anatomy, including a location of the patient's center-of-balance.

23. The method of claim 22, wherein the at least a portion of the patient's skeletal structure includes a substantial portion of the patient's spine.

24. The method of claim 23, wherein the at least one anatomical feature includes the patient's knees.

25. The method of claim 23, wherein the at least one anatomical feature includes one or more of the patient's knees, hips, and shoulders.

26. The method of claim 25, wherein the obtaining balance data includes using a force sensing pad.

27. The method of claim 26, wherein the obtaining position data includes using an electromagnetic measurement system.

28. The method of claim 27, wherein the obtaining position data further includes using a plurality of sensors.

29. The method of claim 28, further comprising determining a treatment plan for the patient.

30. The method of claim 29, monitoring the effectiveness of the treatment plan.

31. The method of claim 30, wherein monitoring the effectiveness of the treatment plan comprises:
obtaining an updated radiographic image of the at least a portion of a patient's skeletal structure;
obtaining updated balance data related to the patient's center-of-balance;
simultaneous with obtaining the updated balance data, obtaining updated position data for the at least one anatomical feature of the patient by monitoring the three-dimensional position of the at least one anatomical feature;
combining the updated balance data and the updated position data with the updated radiographic image; and
comparing the combined updated data and image with the initial combined data and image.

* * * * *